United States Patent
Rasmussen

(10) Patent No.: US 6,995,380 B2
(45) Date of Patent: Feb. 7, 2006

(54) END EFFECTOR FOR SUPPORTING A MICROSAMPLE

(75) Inventor: Jørgen Rasmussen, Beaverton, OR (US)

(73) Assignee: Ascend Instruments, LLC, Beaverton, OR (US)

( * ) Notice: Subject to any disclaimer, the term of this patent is extended or adjusted under 35 U.S.C. 154(b) by 134 days.

(21) Appl. No.: 10/801,521

(22) Filed: Mar. 12, 2004

(65) Prior Publication Data

US 2004/0178372 A1 Sep. 16, 2004

Related U.S. Application Data

(60) Provisional application No. 60/455,071, filed on Mar. 13, 2003.

(51) Int. Cl.
*H01J 27/20* (2006.01)

(52) U.S. Cl. .......... 250/442.11; 250/307; 250/491.1; 250/440.1

(58) Field of Classification Search .......... 250/310, 250/442.11, 307, 306; 345/161; 359/380, 359/385, 388
See application file for complete search history.

(56) References Cited

U.S. PATENT DOCUMENTS

| 4,463,257 | A | * | 7/1984 | Simpkins et al. ........ 250/310 |
| 4,710,633 | A | * | 12/1987 | Suzuki ............ 250/442.11 |
| 5,021,364 | A | | 6/1991 | Akamine et al. |
| 5,036,205 | A | * | 7/1991 | Clement et al. ...... 250/442.11 |
| 5,124,645 | A | * | 6/1992 | Rhoden et al. ........... 324/754 |
| 5,225,683 | A | * | 7/1993 | Suzuki et al. ........ 250/442.11 |
| 5,239,863 | A | | 8/1993 | Kado et al. |
| 5,270,552 | A | | 12/1993 | Ohnishi et al. |
| 5,332,275 | A | * | 7/1994 | Conway et al. ........... 294/100 |
| 5,412,503 | A | * | 5/1995 | Nederlof ................ 359/393 |
| 5,435,850 | A | | 7/1995 | Rasmussen |
| 5,572,026 | A | * | 11/1996 | Ikeda .................. 250/307 |
| 5,698,856 | A | * | 12/1997 | Frasca ............... 250/440.11 |
| 6,002,136 | A | * | 12/1999 | Naeem ............... 250/442.11 |
| 6,027,522 | A | * | 2/2000 | Palmer .................. 606/205 |
| 6,388,262 | B1 | * | 5/2002 | Alani et al. ........ 250/442.11 |
| 6,420,722 | B2 | | 7/2002 | Moore et al. |
| 6,538,254 | B1 | | 3/2003 | Tomimatsu et al. |
| 6,570,170 | B2 | | 5/2003 | Moore |
| 6,614,029 | B2 | | 9/2003 | Asjes |
| 2001/0045511 | A1 | | 11/2001 | Moore et al. |
| 2002/0050565 | A1 | | 5/2002 | Tokuda et al. |
| 2002/0079463 | A1 | | 6/2002 | Shichi et al. |
| 2002/0125427 | A1 | | 9/2002 | Chand et al. |
| 2003/0085354 | A1 | | 5/2003 | Fukuda et al. |
| 2005/0035302 | A1 | * | 2/2005 | Morrison ............ 250/442.11 |

FOREIGN PATENT DOCUMENTS

| JP | 04-274151 | 9/1992 |
| JP | 04-343685 | 11/1992 |
| JP | 05-052721 | 3/1993 |
| JP | 2002-187099 | 7/2002 |

\* cited by examiner

*Primary Examiner*—Nikita Wells
*Assistant Examiner*—Johnnie L Smith, II
(74) *Attorney, Agent, or Firm*—Kolisch Hartwell, P.C.

(57) ABSTRACT

An end effector for supporting a microsample during instrumental analysis, including a generally planar body and a cantilever tip configured to be associated with the microsample.

18 Claims, 6 Drawing Sheets

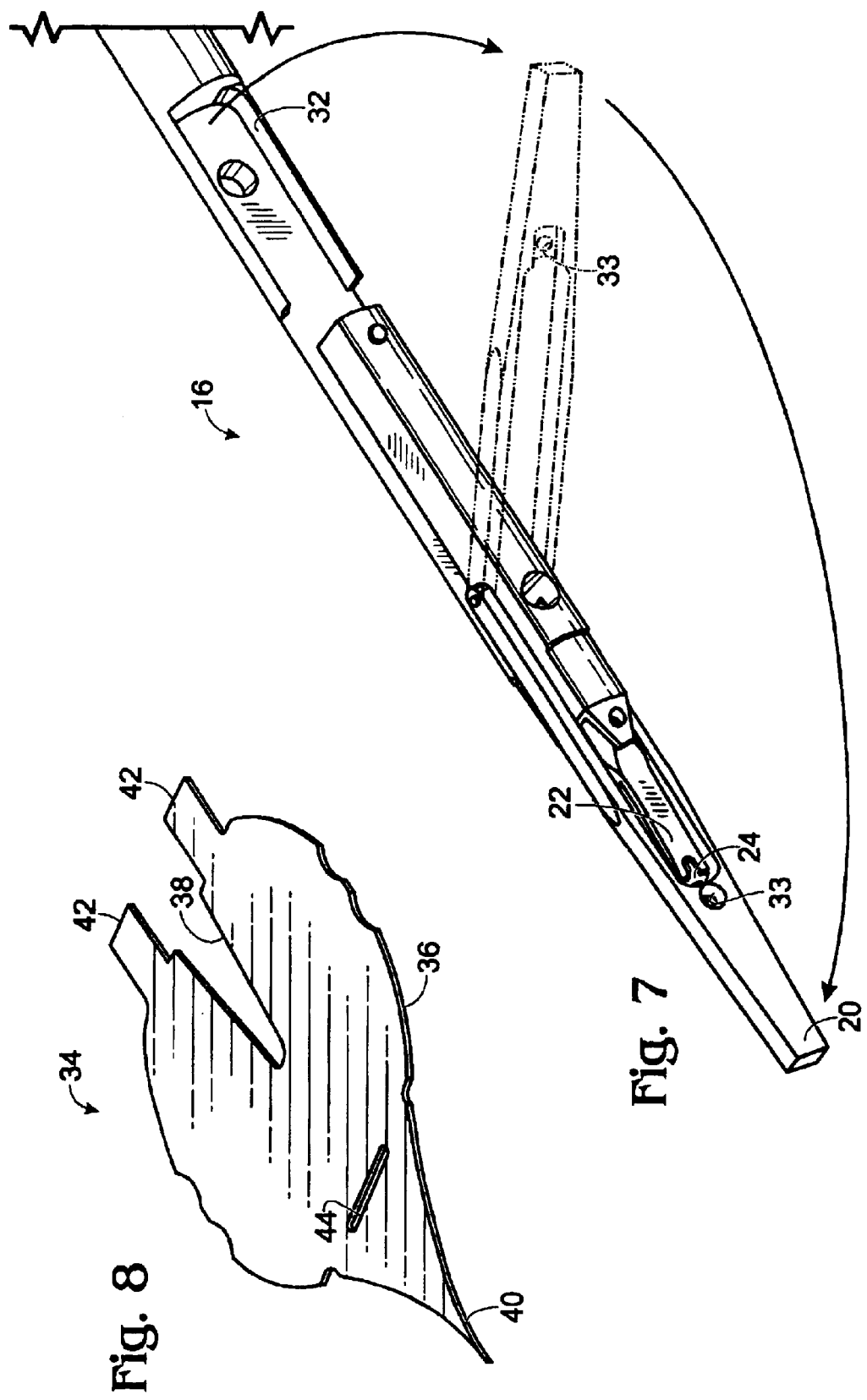

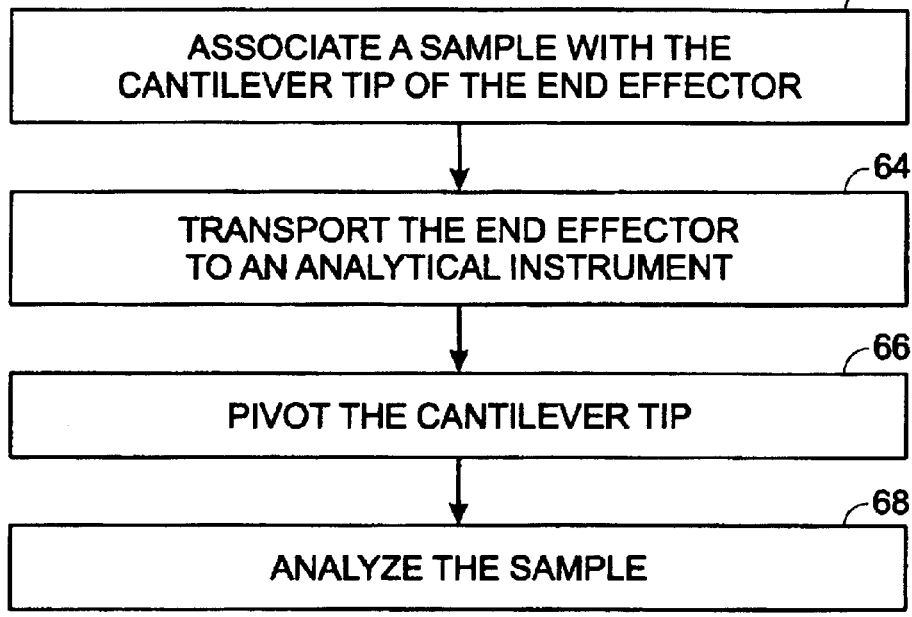
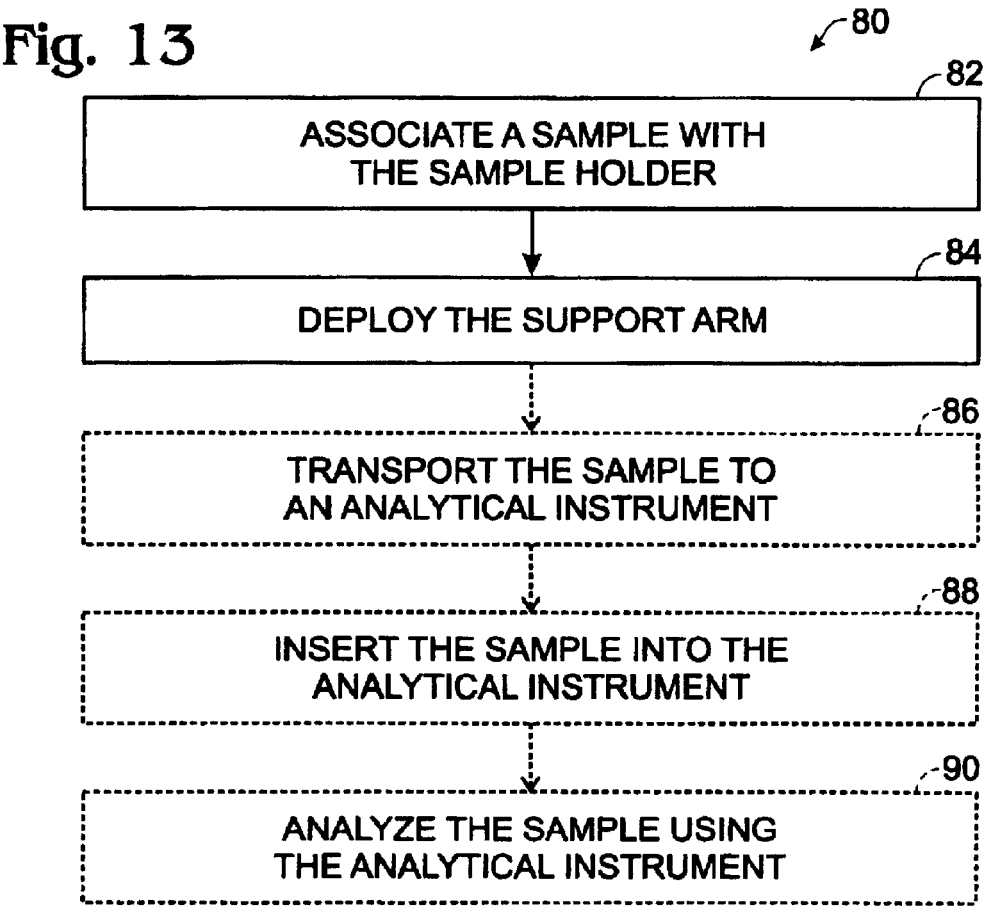

END EFFECTOR FOR SUPPORTING A MICROSAMPLE

This application is based upon and claims benefit under 35 U.S.C. § 119(e) of U.S. provisional patent application Serial No. 60/455,071, filed Mar. 13, 2003, hereby incorporated by reference.

TECHNICAL FIELD

The invention relates to sample manipulation systems useful for instrumental analysis. In particular, the invention relates to sample holders useful for sample manipulation systems in conjunction with instrumental analysis.

BACKGROUND

Electron microscopy, or EM, is a powerful tool for analyzing a variety of samples. EM, which may include Transmission Electron Microscopy (TEM), Scanning Electron Microscopy (SEM), or any combination or variation thereof, may be used to investigate the morphology, crystallograpy, or composition of a sample. That is, EM may reveal the crystallographic, physical or chemical composition of a sample, while examining a sample area only a few nanometers in diameter.

During nanotechnology processes, and as an aid to manufacturing, it may be desirable to analyze samples from large arrays of devices using EM to insure the quality of the manufacturing process. As an aid to bioengineering, it may be desirable to pick up cells or molecules for physical or chemical processing. For example, a focused ion beam (or FIB) system may be used to cut a small sample from a semiconductor wafer for analysis. Using a sample extraction device, the resulting sample may be transferred to a sample holder, and loaded into a microscope. As the sample is typically very small, appropriate sample preparation and placement can be both delicate and time-consuming. The necessary manipulation of the sample may create a substantial risk of damaging or losing the sample entirely, and even a skilled operator may have only one opportunity to place the sample correctly.

The ability to collect, transport, and place very small samples using an improved sample manipulation system would benefit a variety of analytical methods, including EM, Auger spectroscopy, reactive ion etching, SIMS, ESCA, CVD, ion implantation, and plasma deposition, among others.

BRIEF DESCRIPTION OF THE DRAWINGS

FIG. 7 is a perspective view of the underside of the distal tip of the sample manipulator of FIG. 1, showing the support arm in a deployed position.

FIG. 8 is an isometric view of an end effector according to an embodiment of the present invention.

FIG. 12 is a flowchart demonstrating a method of using an end effector according to an embodiment of the present invention.

FIG. 13 is a flowchart demonstrating a method of using a sample manipulator according to an embodiment of the present invention.

DETAILED DESCRIPTION

Figure 1:
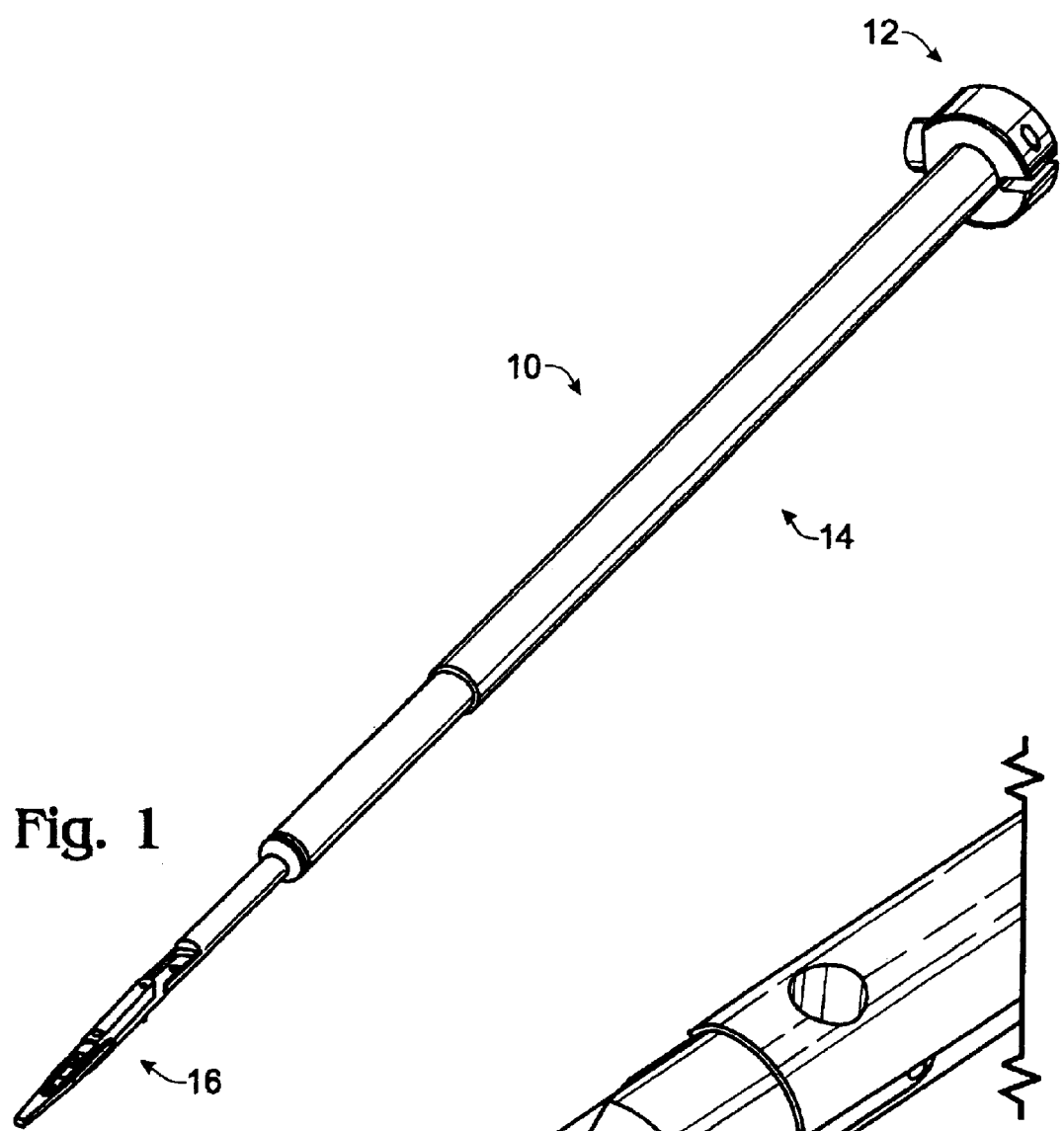
FIG. 1 is a perspective view of a sample manipulator, according to an embodiment of the present invention.
Figure 2:
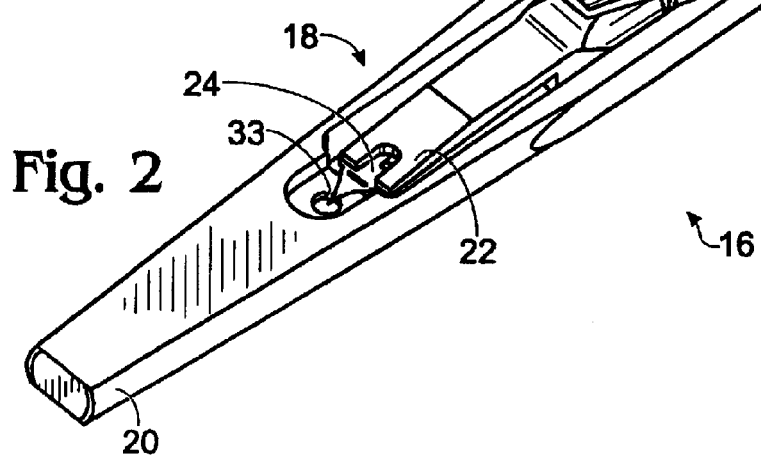
FIG. 2 is a perspective view of a distal tip of the sample manipulator of FIG. 1, with a support arm in a deployed position.

A sample manipulator 10 for a sample manipulation system is shown in FIG. 1, with the ventral surface (underside) of the sample manipulator facing upwards. The sample manipulator is generally configured to collect and/or transport a sample for subsequent instrumental analysis. Sample manipulator 10 may include a proximal end 12, a shaft 14, and a distal end 16. The distal end 16 may include a sample holder 18, as shown in FIG. 2 with the ventral surface facing downwards. The sample holder typically is configured to retain a collected sample securely during transportation of the sample, and may facilitate the presentation of the sample in an appropriate position and orientation for instrumental analysis and/or evaluation. The sample holder may be removable from the sample manipulator, in order to facilitate transfer of a sample from a first sample manipulator to a second sample manipulator. The sample holder is typically configured to facilitate sample collection, sample transportation, and/or sample analysis for a variety of microsamples, or very small samples, in a variety of applications, and so may be useful in conjunction with any type of instrument or analytical method that may benefit from efficient and accurate sample manipulation, including microscopes, spectrometers, and other instruments, among others.

As shown in FIG. 2, distal tip 16 of the sample manipulator may include sample holder 18 and a support arm 20, where the sample holder may include a clamp 22 configured to reversibly affix a sample platform 24. Sample holder 18 may be configured to be axially removable from the distal end of sample manipulator 10. That is, sample holder 18 may be removed from sample manipulator 10, and then associated with a second sample manipulator, which may have the same or different configuration as sample manipulator 10. In one aspect, the sample holder may include a portion that is inserted into a corresponding recess in the distal end of the sample manipulator shaft. The sample holder may be retained by frictional forces, or by a retention mechanism such as a set screw, a clip, or other retaining device.

Any sample platform that facilitates placement and attachment of a desired sample and is configured to be compatible with sample holder 18 is a suitable sample platform. Additionally, the sample platform used typically is configured for compatibility with the particular analytical method intended to be used. For example, when used in conjunction with transmissive methods, such as electron microscopy, the sample platform is typically configured to permit the electron beam to pass through a sample of interest without being blocked by the sample holder or the sample platform. The sample platform may be configured so that a sample of interest may be associated with the sample platform using any of a variety of attachment methods, including but not limited to mechanical friction (such as applied by a clamp or tweezers), static attraction, and ion beam deposit for example as described in U.S. Pat. No. 5,435,850 to Rasmussen (1995), hereby incorporated by reference.

The sample platform may be substantially planar. For example, the sample platform may include a planar perforated or solid disk. The sample platform may incorporate a grid, such as is typically used in electron microscopy. The sample platform may include carbon or a metal such as copper or gold, among others. In particular, the sample platform may include a disk that is circular in shape, and may have a diameter of approximately 3 mm, as is typical for TEM sample platforms.

The sample platform may be reversibly retained by a sample holder that includes a clamp 22. Any clamp that is configured to reversibly affix the sample platform for analysis is a suitable clamp for the sample manipulator. By reversibly affix is meant that the sample platform may be substantially secured by the clamp, and yet be removable when desired. The clamp may incorporate a compressive retention mechanism, such as a 'tweezing' action. The sample platform may be associated with the clamp, for example, by opening the tweezing element of the clamp with a tool or probe, inserting the sample platform, and permitting the clamp to fasten upon the sample platform. Alternatively, the clamp may open in a 'scissor-like' motion, wherein the clamp is scissored open, the sample platform is inserted into the clamp, and the clamp is then scissored closed again.

Figure 3:
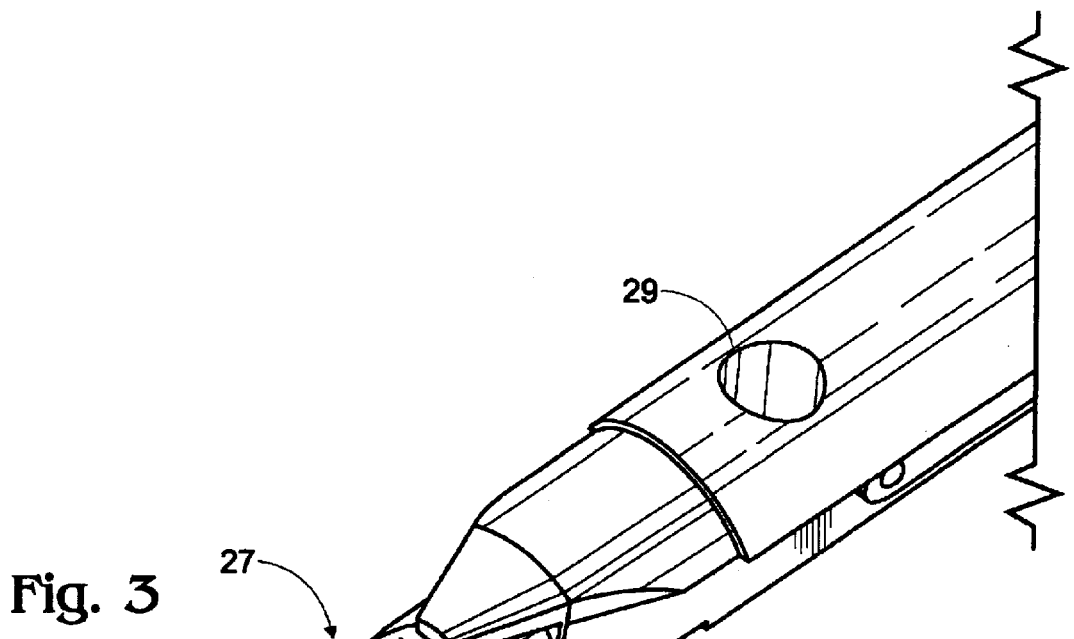
FIG. 3 is a perspective view of a distal tip of a sample manipulator according to another embodiment of the present invention, with the support arm in a retracted position.
Figure 4:
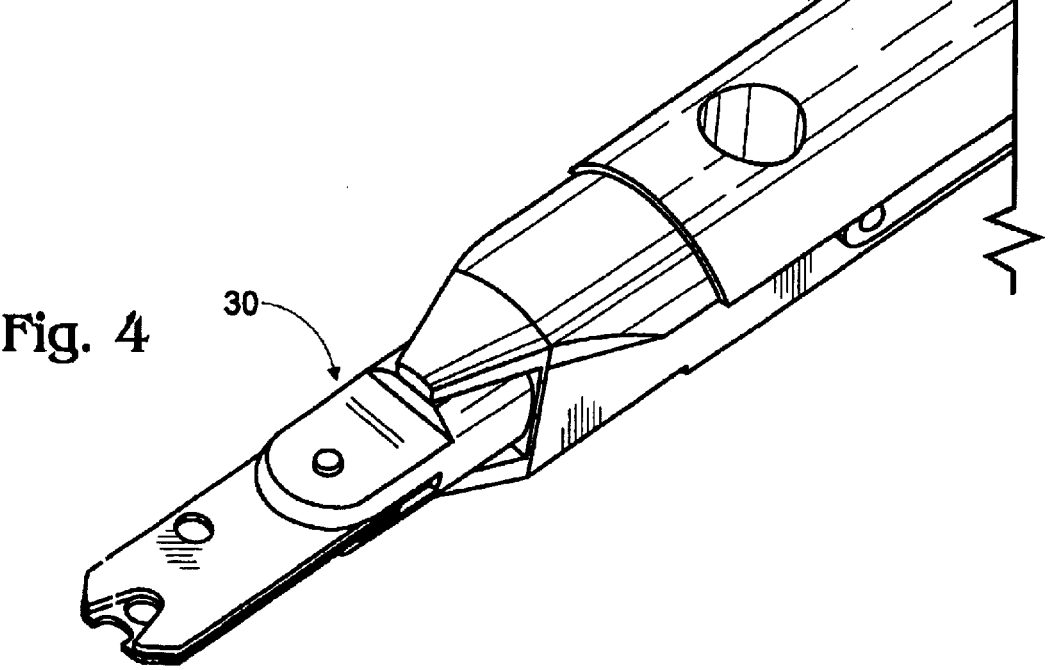
FIG. 4 is a perspective view of a distal tip according to an alternative embodiment of the present invention.
Figures 5, 6:
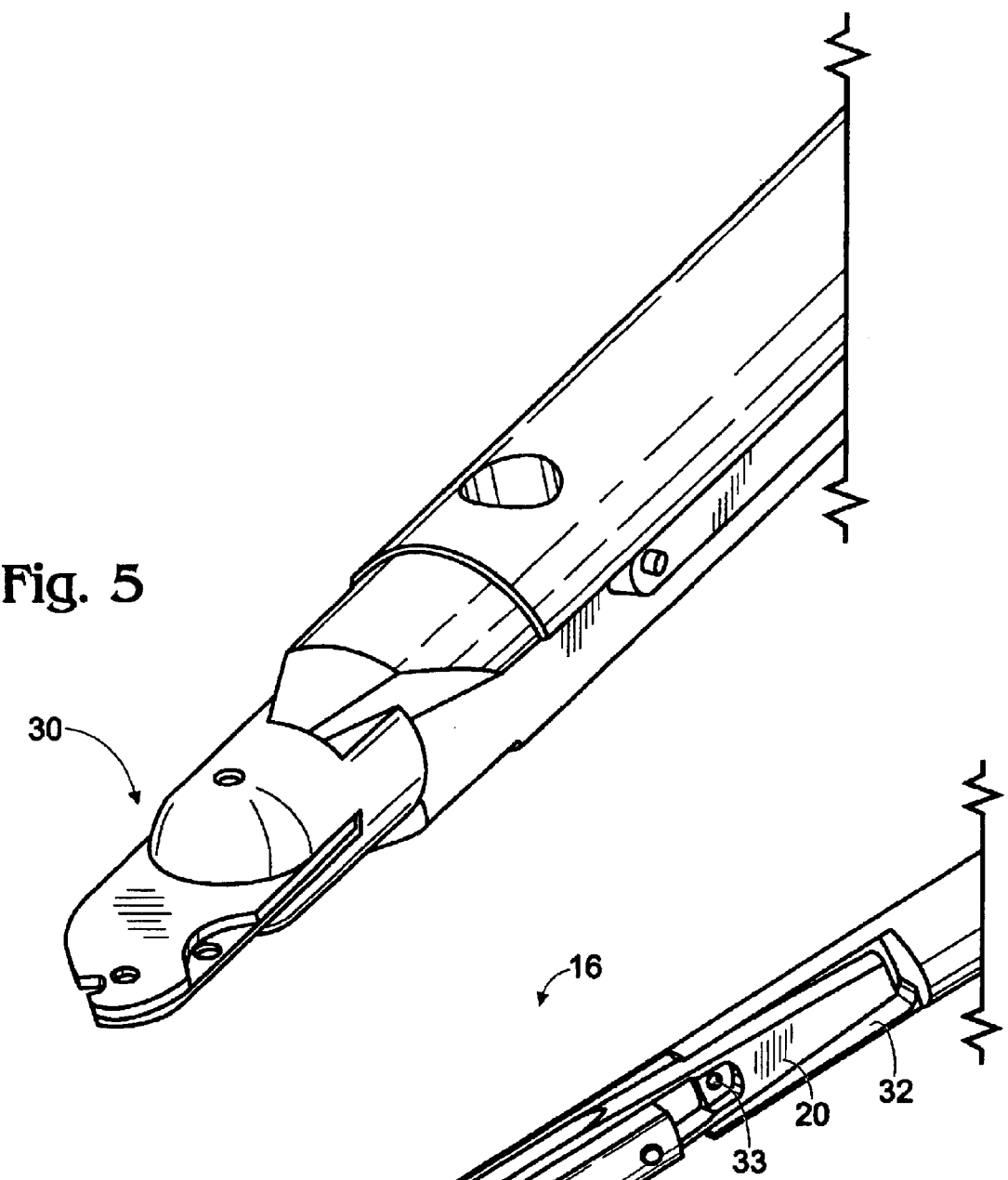
FIG. 5 is a perspective view of a distal tip according to another alternative embodiment of the present invention.
FIG. 6 is a perspective view of the underside of the distal tip of the sample manipulator of FIGS. 1 and 2, showing the support arm in a retracted position.

For example as shown in FIG. 3, sample holder 26 includes a clamp 27 that is associated with a sample platform 28. Sample holder 26 is removably affixed to the shaft of the sample manipulator, and is retained using a set screw (not shown) within aperture 29. FIGS. 4 and 5 show alternative suitable sample holders 30 and 31 that may be compatible with a variety of sample platforms. Any appropriate combination of sample manipulator shaft, sample holder, and sample platform may be used to transport a sample, for example from instrument to instrument. In a particular example, the sample manipulation system described herein may be useful in combination with the sample preparation apparatus described in U.S. patent application Ser. No. 09/920,715, filed Aug. 3, 2001, hereby incorporated by reference.

Support arm 20, when present, typically is placed in a retracted position before the distal tip 16 is used to collect a sample of interest. For example, as shown in FIG. 6, support arm 20 may be rotated into a position along the underside of the sample manipulator, for example in a recess 32. With the support arm retracted, the sample manipulator may be inserted into an instrument, such as a FIB system for example, in order to collect the sample of interest. After the device is inserted into the FIB system, the sample of interest may be attached to or otherwise associated with the sample platform. Upon collecting the sample, the sample manipulator may be removed from the instrument, and the support arm may be moved from the retracted position to a deployed position, as shown from the underside of the sample manipulator in FIG. 7. The support arm may be deployed by sliding, rotating, pivoting, or otherwise urging the support arm from the retracted position to the deployed position. As shown in FIGS. 6 and 7, the support arm may be deployed by pivoting the support arm.

When the support arm is in the deployed position, the sample holder may be substantially supported and/or protected from damage by the support arm, and yet remain accessible for the desired instrumental analysis. In this way, the sample itself is protected and supported during transport of the sample. Support arm 20 may incorporate an aperture 33 that aligns with at least a portion of the sample holder so that a desired analysis may be performed. For example a transmissive analytical method, such as transmission electron microscopy, that relies upon passage through the sample may be performed on the sample while the support arm is in the deployed position, as shown in FIG. 2.

Typically, the sample manipulator is configured so that the distal tip of the manipulator may be inserted directly into an EM or other instrument for further analyses of the sample. In particular, the distal tip may be inserted into the desired instrument with the support arm in the deployed position to protect and/or support the sample holder. Alternatively, the distal tip may be inserted into the desired instrument with the support arm retracted, to offer greater access to the sample of interest. The sample insertion process may be reversed if additional milling or shaping of the sample is desirable. That is, the sample manipulator may be removed from the instrument and reinserted into an FIB system, for example, for further shaping. The support arm may be deployed during transport to the FIB in order to support and/or protect the sample.

In another aspect, a first sample manipulator may be used in conjunction with a sample holder to associate a sample with a sample platform. The sample holder may then be removed from the first sample manipulator and transferred to a second sample manipulator, without disturbing either the sample platform or the associated sample. In this manner, samples may be easily transferred to and from specialized sample manipulators useful for individual instruments, without manipulating the sample itself. In a particular example, a sample may be collected in an FIB, then the sample holder may be transferred to a second sample manipulator that is configured for insertion into an EM for analysis.

End Effector

Sample manipulator 10 may be used in conjunction with a sample platform that is an end effector 34, as shown in FIG. 8. The end effector may have any suitable geometry and orientation. End effector 34 may include a generally planar body 36 that defines an aperture 38, and that includes a cantilever sample tip 40. End effector body 36 may be sized to be compatible with existing sample holders. For example, where end effector body is generally disk-shaped, the end effector disk may have a diameter of about 3 mm in order to readily placed and retained in a conventional TEM sample holder.

End effector 34 may be fabricated using conventional chemical etching or photoetching methods, and may exhibit any desired shape or geometry. The end effector may be prepared using any material that exhibits the requisite combination of stiffness and flexibility, although it may be preferable to select a material that is distinct from potential sample compositions, so as to help avoid erroneous analytical results. Typically the end effector may be prepared from a ductile metal.

Figure 9:
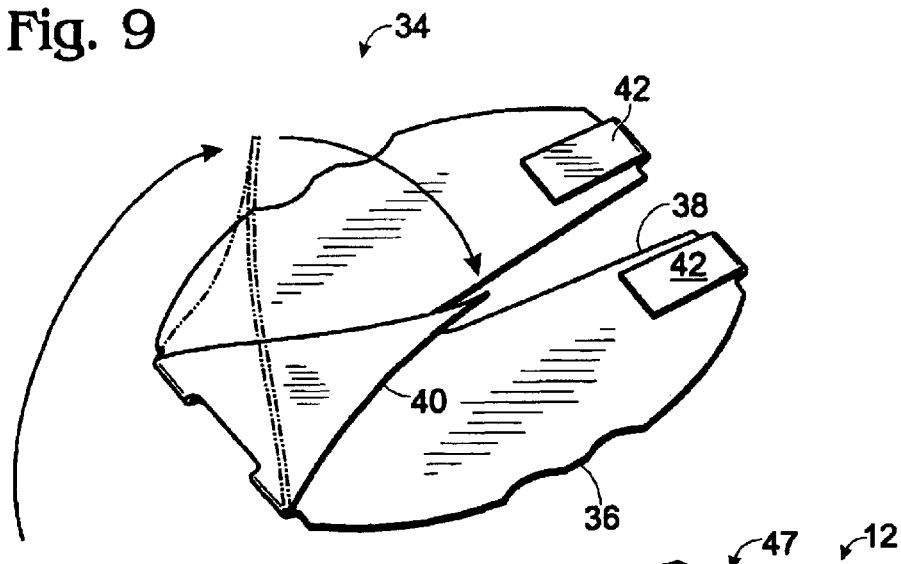
FIG. 9 is an isometric view of the end effector of FIG. 8, showing the sample tips and tabs folded.

As shown in FIG. 8, end effector 34 may be fabricated to exhibit a planar geometry. The end effector may include one or more tabs 42 that may be folded over to provide a region of greater thickness to be engaged by the clamp of the sample holder, as shown in FIG. 9. Cantilever tip 40 may possess a sharp point, a rounded tip, a flat tip, a knife edge, or any other geometry that facilitates placement and attachment of a desired sample. As the sample of interest may be very small, the geometry of the sample tip may be precisely shaped, for example using acid electrolysis.

End effector body 36 and cantilever tip 40 are typically integrated in a single unit. The sample of interest may be attached to and/or associated with the sample tip for transport and/or analysis. As described above, the sample may be attached to the cantilever tip using gas welding techniques, adhesives, chemical bonding, or any other appropriate method of attachment that does not interfere with subsequent analyses. The end effector may be configured so that when placed in the sample holder, and the support arm is deployed, the cantilever tip of the end effector is aligned with an aperture in the support arm.

Where additional rotational freedom is desired in order to more properly analyze the sample, the end effector may be configured to permit the cantilever tip to be pivoted or folded to one or more additional configurations. For example, where a particular sample angle is desired, the cantilever tip may be gently flexed, or bent, using an appropriate tool to obtain the desired sample positioning. Alternatively, or in addition, the end effector may include an integrated fold line 44. The integrated fold line may permit the sample tip to be folded up to 180 degrees with respect to the end effector body, thereby bringing the sample tip (and therefore the attached sample) into alignment with aperture 38, as shown in FIG. 9. Aperture 38 may be a circular void, slot, or other opening in the planar body. Alternatively, the aperture may extend to and intersect with the edge of the planar body, forming a notch. Such a notch may be rectangular, wedge shaped, or rounded. Any opening that permits transmissive analysis of the sample to be performed with the cantilever tip folded is a suitable aperture. Alternatively fold line 44 may be defined by a thinning of the planar body material along the desired fold line, without the formation of an aperture.

Once folded, the end effector may be sized to be compatible with conventional sample holders. For example, the end effector body may include a disk having a diameter of about 3 mm, so that the folded end effector may be placed and retained in a conventional sample holder, such as a double-tilt sample holder. In addition to facilitating surface analysis, the presence of aperture 38 may permit various transmissive analyses, such as by TEM, or further shaping of the sample using an FIB system, even with the cantilever tip folded.

Sample Manipulator Housing

Figure 10:
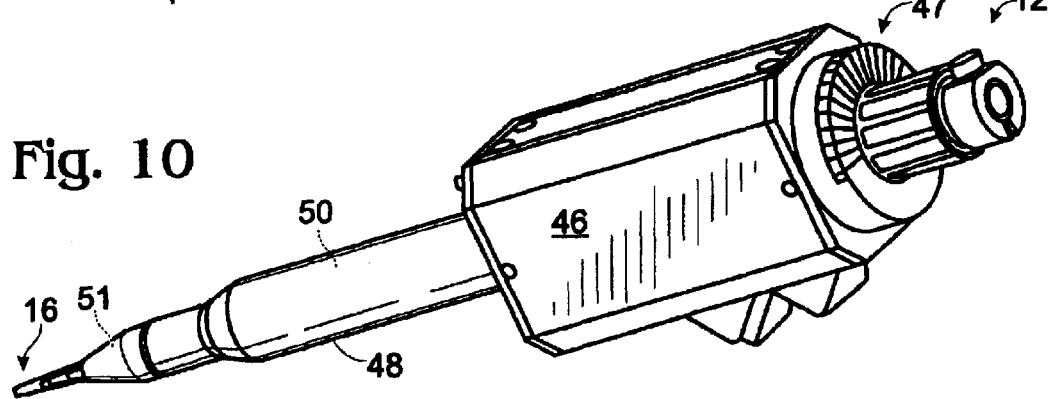
FIG. 10 is a perspective view of a sample manipulator housing, according to an embodiment of the present invention.

Sample manipulator 10 may be incorporated in, and used in conjunction with, a manipulator housing 46, as shown in FIG. 10. The manipulator housing may be configured to facilitate access to the sample chamber of an instrument, and may be associated with the instrument itself. The sample manipulator housing may be configured so that the sample manipulator may be inserted into the manipulator housing, so that the housing at least partially encloses the sample manipulator. When fully inserted, the manipulator housing typically permits access to distal end 16 of the sample manipulator, and therefore permits access to the sample of interest. Typically, the manipulator housing is configured so that when the distal end of the sample manipulator extends from the sample manipulator housing, the distal end is within an instrument chamber. The manipulator housing may be configured to permit access to the sample when the support arm is in the retracted position, the deployed position, or both.

In order to assist in precise sample placement for analysis, the manipulator housing may include one or more motors and/or micro manipulators 47 that permit a user to steer the sample to a desired location and/or desired orientation. The manipulator housing may include a shaft housing 48, that may include an internal vacuum valve 50 adapted to evacuate the interior of the shaft housing. The manipulator housing may further incorporate a distal port 51.

Figure 11:
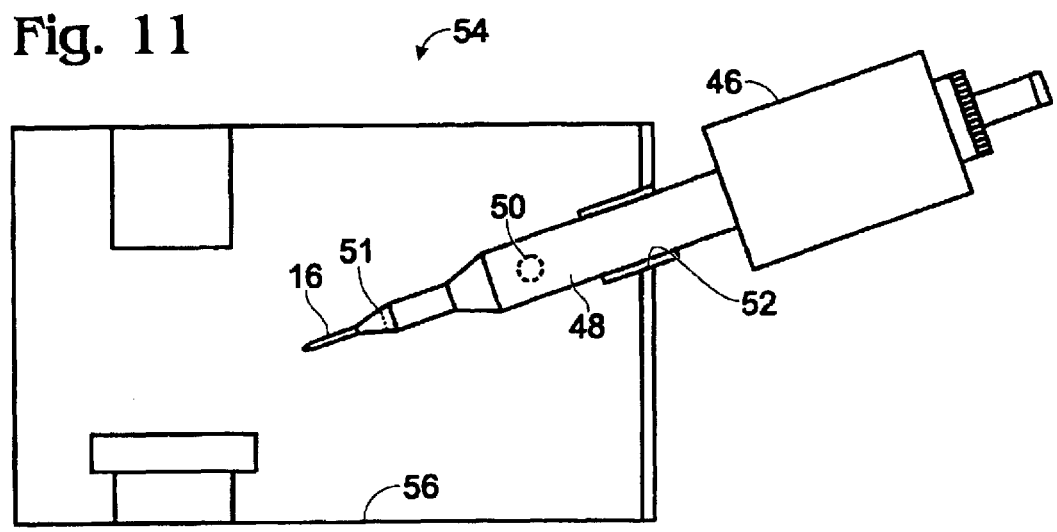
FIG. 11 is a schematic showing the insertion of the sample manipulator housing of FIG. 10 into an instrument.

For example as shown in FIG. 11, manipulator housing 46 may be inserted into and engaged with an access port 52 of an appropriate instrument in an airtight manner. The sample manipulator may be inserted into the sample manipulator, sealed from contact with the external atmosphere, and vacuum valve 50 located in the shaft housing may then be opened to quickly evacuate, or "rough out" the interior of the shaft housing 48. Once the interior of the housing is substantially evacuated, distal port 51 may be opened to provide access to the interior of vacuum chamber 56 of, for example, a FIB system, EM system, or other instrument. Once port 51 is open, the distal end 16 of the sample manipulator may be inserted completely into vacuum chamber 56, and the sample may be oriented and placed appropriately for sample collection, manipulation, and/or analysis.

Where the instrument is used for sample collection, the sample manipulator and manipulator housing may be used to collect a sample of interest by permitting the end effector cantilever tip to be positioned precisely over the sample of interest, and perform the lift-out of the sample quickly and efficiently.

The sample manipulator and/or sample manipulator housing also may include any of a variety of additional tools, instruments, or detectors that may be configured to facilitate sample collection, sample transport, or sample characterization. For example, the sample manipulator may include a current measurement attachment, thereby making it useful as a test and measurement tool. Alternatively, or in addition, the sample manipulator may include micro tweezers for the manipulation of small parts, such as may be required for extracting or repairing Micro-Electromechanical Systems (or MEMS) devices in a FIB system, among others. Alternatively or in addition, laser marking of the sample may be facilitated by including an objective optical lens in association with the manipulator housing, for example mounted in front of the sample manipulator. Laser marking may also be facilitated by the presence of one or more motors and/or micro manipulators, as described in connection with the manipulator housing, above. Other devices may also be inserted into an instrument system in conjunction with the sample manipulator or sample manipulator housing, such as electromechanical tweezers, gas injection needles, optical microscopes (bore scopes), signal detectors, among others.

Additional suitable microinstruments and/or microtools may include an FIB source, a cutting laser source, or a micro cutting tool, among others. Suitable detectors include radiation detectors, including photodetectors. The sample manipulator may permit such associated devices to be inserted beneath the electron beam in an EM.

In a particular example, the sample manipulator may be used in conjunction with a detector located under the sample. The sample manipulator may be used as a trimming and imaging stage in a dual beam system. The FIB may be used to thin the sample. Rotation of the sample perpendicular to the electron beam may permit formation of a transmission image of the sample.

The end effector described herein lends itself to a method of use as set out in the flowchart 60 of FIG. 12. In particular, the method includes, but is not limited to, associating a sample with the cantilever tip (62), pivoting the cantilever tip (64), transporting the end effector to an analytical instrument (66); and analyzing the sample (68). The cantilever tip may be pivoted before or after transport to the analytical instrument.

The sample manipulator described herein lends itself to a method of use as set out in the flowchart 80 of FIG. 13. In particular, the method includes, but is not limited to, associating a sample with the sample holder (82), and deploying the support arm (84). The method may also further include one or more of transporting the sample to an analytical instrument (86), inserting the sample into the analytical instrument (88), and analyzing the sample using the analytical instrument (90). The method may also further include retracting the support arm before inserting the sample holder into the analytical instrument (92).

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

What is claimed is:

1. An end effector configured to support a microsample for instrumental analysis, comprising:
    a generally planar body including an aperture; and
    a cantilever tip pivotally extending from the planar body, the cantilever tip being configured to be associated with the microsample such that pivoting the cantilever tip brings the cantilever tip substantially into alignment with the aperture.

2. The end effector of claim 1, wherein the planar body is generally disk-shaped.

3. The end effector of claim 1, wherein the cantilever tip is pivotal up to about 180 degrees with respect to the planar body.

4. The end effector of claim 1, wherein the aperture includes a notch in the planar body.

5. The end effector of claim 4, wherein the end effector includes an integrated fold line that facilitates pivoting the cantilever tip.

6. The end effector of claim 4, wherein the integrated fold line includes an elongate aperture.

7. The end effector of claim 1, wherein the cantilever tip includes a sharp point.

8. The end effector of claim 1 wherein the planar body includes a disk having a diameter of about 3 mm.

9. The end effector of claim 1, wherein the end effector is formed by chemical etching or photoetching.

10. The end effector of claim 1, wherein the end effector is formed of a ductile metal.

11. The end effector of claim 1, further comprising a microsample holder configured to reversibly couple to the end effector.

12. The end effector of claim 11, wherein the microsample holder includes a clamp.

13. The end effector of claim 11, further comprising a microsample manipulator that includes a shaft having a proximal end and a distal end, wherein the microsample holder is associated with the distal end.

14. The end effector of claim 13, wherein the microsample holder is axially removable from the distal end of the shaft.

15. The end effector of claim 11, wherein the end effector and the microsample holder are configured to permit transmission through an associated microsample during instrumental analysis.

16. A method of using an end effector having a generally planar body, and a cantilever tip associated with the planar body; comprising:
    associating a sample with the cantilever tip;
    transporting the end effector to an analytical instrument;
    pivoting the cantilever tip; and
    analyzing the samples;
    wherein the end effector includes an aperture in the planar body, and pivoting the cantilever tip brings the sample substantially into alignment with the aperture.

17. The method of claim 16, wherein the sample is associated with the cantilever tip using a focused ion beam system.

18. The method of claim 16, wherein the sample is analyzed using transmission electron microscopy.

* * * * *